(12) United States Patent
Börmann et al.

(10) Patent No.: US 7,947,147 B2
(45) Date of Patent: May 24, 2011

(54) NONWOVEN/FILM LAMINATES

(75) Inventors: Ludwig Börmann, Babensham (DE); Günter Schreiner, Schnaitsee (DE)

(73) Assignee: RKW SE, Frankenthal/Pfalz (DE)

( * ) Notice: Subject to any disclaimer, the term of this patent is extended or adjusted under 35 U.S.C. 154(b) by 798 days.

(21) Appl. No.: 11/574,535

(22) PCT Filed: Aug. 17, 2005

(86) PCT No.: PCT/EP2005/008903
§ 371 (c)(1),
(2), (4) Date: Apr. 3, 2007

(87) PCT Pub. No.: WO2006/024394
PCT Pub. Date: Mar. 9, 2006

(65) Prior Publication Data
US 2007/0254158 A1    Nov. 1, 2007

(30) Foreign Application Priority Data
Sep. 2, 2004    (DE) .......... 10 2004 042 405

(51) Int. Cl.
*B32B 37/04* (2006.01)
(52) U.S. Cl. ........ 156/309.6; 156/229; 156/244.11; 156/244.16; 156/277; 156/308.2; 156/324
(58) Field of Classification Search .......... 156/242, 156/244.11, 244.16, 244.24, 309.9, 500, 156/501, 308.2, 309.6, 229, 277, 324
See application file for complete search history.

(56) References Cited

U.S. PATENT DOCUMENTS

| | | | | |
|---|---|---|---|---|
| 3,622,422 A | * | 11/1971 | Newman | 156/309.6 |
| 3,627,613 A | * | 12/1971 | Stolki | 156/309.6 |
| 3,639,199 A | * | 2/1972 | Brandts et al. | 428/110 |
| 4,088,805 A | * | 5/1978 | Wiegand | 442/370 |
| 4,109,543 A | * | 8/1978 | Foti | 198/847 |
| 4,367,312 A | * | 1/1983 | Bontinck et al. | 525/93 |
| 5,256,231 A | * | 10/1993 | Gorman et al. | 156/178 |
| 5,571,364 A | * | 11/1996 | Suzuki et al. | 156/309.6 |
| 5,656,119 A | * | 8/1997 | Srinivasan et al. | 156/290 |
| 5,695,868 A | | 12/1997 | McCormack | |
| 5,766,710 A | * | 6/1998 | Turnlund et al. | 623/1.15 |
| 5,837,352 A | | 11/1998 | English et al. | |
| 5,865,926 A | | 2/1999 | Wu et al. | |
| 5,879,614 A | | 3/1999 | Harrison | |

FOREIGN PATENT DOCUMENTS

| | | |
|---|---|---|
| DE | 195 38 049 A1 | 4/1997 |
| EP | 0 650 828 A1 | 5/1995 |
| EP | 0 768 168 A2 | 4/1997 |
| EP | 0 841 156 A1 | 5/1998 |
| WO | WO 94/20298 A1 | 9/1994 |

* cited by examiner

*Primary Examiner* — Kat Wyrozebski
*Assistant Examiner* — Scott W Dodds
(74) *Attorney, Agent, or Firm* — Paul D. Strain; Strain & Strain PLLC

(57) ABSTRACT

The invention relates to a method for producing nonwoven/film laminates for personal hygiene articles, from an initial film web consisting of a thermoplastic polymer and an initial nonwoven web. According to said method, the initial film web and the initial nonwoven web, whose melting point lies above the crystallite melting point of the polymer, are heated to a temperature that exceeds the crystallite melting point of the polymer and lies below the melting point of the initial nonwoven web. The laminate is then guided through a cooled nip and is cooled to a temperature that lies below the crystallite melting point of the initial film web. The invention also relates to laminates that can be produced by said method.

7 Claims, 1 Drawing Sheet

NONWOVEN/FILM LAMINATES

Figure 1:
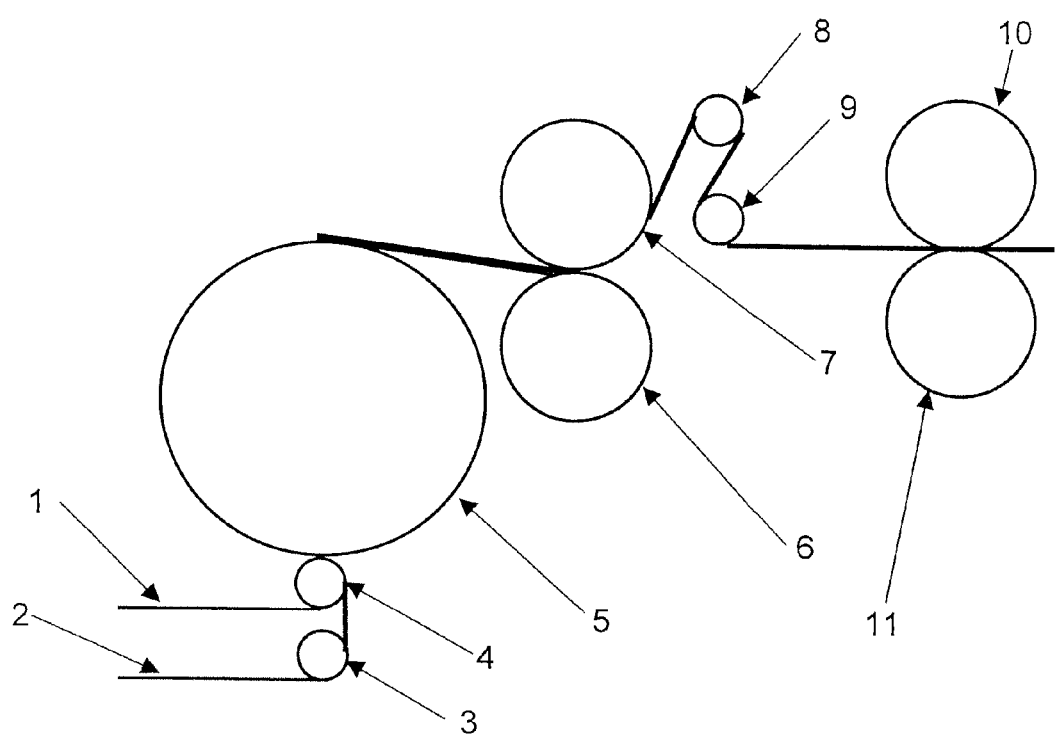

The invention relates to improved nonwoven-film laminates and to a method for the production thereof.

Being a waterproof material and, if desired, a material that is breathable at the same time, plastic films have become indispensable in a multitude of technical fields and daily life. An broad field of application relates to personal hygiene articles, such as diapers.

While known films meet the requirements for tightness, lightness and breathability to a satisfactory extent, their stability and, above all, their surface condition which is also referred to as "grip" fail to be optimal. In particular, breathable films exhibit poor tear resistance, and the use of thicker and, thus, more stable films increases the cost incurred. As regards the grip, the smooth glossy surface of plastic films is felt to be unpleasant. Particularly the internal surface of personal hygiene articles, which is sitting directly on the skin, and the external surface as well should be felt to be soft and, if possible, give a feeling similar to textile. Smooth films give the impression of clinging to the skin, even if they are breathable films.

A further problem is the development of noise, also referred to as "rustling", which is, in particular, caused by thin films in personal hygiene articles during movements of the wearer. Such rustling should be avoided as far as possible since, otherwise, the acceptance of the personal hygiene article would be impaired.

In order to overcome the above problems, innumerable suggestions have been made for a modification of the films as such and also for the application of laminates made of films containing woven or nonwoven fabrics.

For example, DE 195 38 049 describes a method for the production of a film web which, on the one hand, exhibits improved transverse elasticity and puncture resistance and, on the other hand, improved softness and reduced rustling. Therein, an initial film web consisting of a thermoplastic polymer is heated up to the molten state and above the crystallite melting point of the polymer by means of one or more heating cylinders and is subsequently guided through a cooled nip.

Wide-spread use is also made of laminates consisting of nonwoven or woven fabrics or films, since these combine the waterproofness of the film with the textile like surface of woven or nonwoven fabrics. Nonwoven fabrics are used primarily. In the most simple case, the laminates consist of a film and a nonwoven fabric, which can be combined with each other in various manners. Thermobonding, adhesive bonding and direct extrusion (cast method) are the most current methods.

In thermobonding, a stamping roller (=engraved steel roller) is used, mostly together with a smooth steel roller as a second roller, to fuse the material of the film and/or nonwoven fabric in a localized manner by means of high temperature and pressure, with the result that the two material webs are bonded to each other. The method has the disadvantage that, owing to the conditions prevailing during bonding, the film may be damaged and may, therein, lose its liquid tightness, this also being referred to as pinholing. In addition, the bonds are only localized, this having an adverse effect on the composite strength.

U.S. Pat. No. 5,837,352 discloses an example, describing laminates consisting of a film and nonwoven fabric, which may be bonded through thermobonding or ultrasonic or other methods.

Although with adhesive bonding there is achieved a bonding across the entire surface, it results in a deterioration of the breathability of breathable films. What is more, bonding agents cause additional cost and are, in part, suspected of being harmful to health. If, however, localized bonding instead of full-surface bonding is chosen in order to preserve breathability, the composite strength will suffer.

As an alternative to adhesive bonding, films and/or nonwoven layers may be provided or additives may be introduced in the film and/or nonwoven, this allowing bonding at substantially lower temperatures, if the thermobonding method is used. U.S. Pat. No. 5,695,868 describes an example, where a component referred to as bonding agent is contained in either the film or the nonwoven or even in both. This component allows thermobonding below the melting point of the film and nonwoven, with the result that the breathability of the film is preserved, and bonding remains localized.

Direct extrusion is a cost-effective method for non-breathable laminates, ensuring a reliable compound strength, but causing poor softness and a high pinholing risk. If breathable laminates are desired, breathability can only be achieved in a second step through reworking of the composite. For this purpose, either fillers causing the formation of pores thereon when the laminate is stretched are contained in the film, or the laminate is provided with pores through needling.

For example, U.S. Pat. No. 5,865,926 discloses a film which is extruded on a nonwoven web and, subsequently, the composite is stretched (ring-rolled) by means of surface-textured rollers in order to make the composite breathable.

Finally, use is also made of methods where nonwoven fabrics are provided with a coating, in order to achieve the desired tightness against liquids with simultaneous permeability to water vapor. An example thereof is described in U.S. Pat. No. 5,879,341.

None of the known methods is able to meet all requirements in an optimum manner. For that reason, there is a constant demand for improved laminates and improved methods for the production of laminates.

Surprisingly, it has now been found that laminates with excellent breathability, softness and rustling values can be produced by heating a film up to the molten state and combining said film with a nonwoven at this temperature and by then guiding the composite through a cooled nip.

Thus, the aforementioned problems are solved by a method for the production of a laminate from an precursor film web and a precursor nonwoven web, wherein the precursor film web consisting of a thermoplastic polymer and the precursor nonwoven web whose melting point is in excess of the crystallite melting point of the polymer are heated up to a temperature above the crystallite melting point of the polymer, with the laminate then being guided through a cooled nip. The aforementioned problems are also solved by laminates produced by said method.

Surprisingly, the molten polymer of the film web adheres to the non-molten nonwoven web. This composite is fixed in the subsequent cooled nip.

FIG. 1 is a schematic diagram of the thermal lamination method according to the invention.

The precursor film web is produced in known manner, e.g. by blow extrusion. In general, all thermoplastic polymers can be used as materials for the film. A multitude of commercial products is available on the market. Preferably, use is made of LDPE (low density polyethylene), LLDPE (linear low density polyethylene), MDPE (medium density polyethylene), HDPE (high density polyethylene), and various PPs (polypropylene) as well as copolymer of ethylene or propylene with other comonomers. These polymers are either used in their pure form or as polymer mixtures. Usual formulations for hygiene films are, for example, mixtures of 10 to 90% by weight of LDPE, 10 to 90% by weight of LLDPE and 0 to 50% MDPE, such as a mixture of 80% LDPE, 20% LLDPE and pigments meeting the particular requirements. Commercial polymers for hygiene films have the melting ranges or crystallite melting points listed below:

LDPE=112 to 114° C.
LLDPE=119 to 125° C.
MDPE=125 to 128° C.

Usually, hygiene films are dyed, e.g. white with titanium dioxide. In addition, they are provided with usual additives and processing agents, some of which are the molder's trade secret.

Further suitable substances are ethylene vinyl acetate (EVA), ethylene acrylate (EEA), ethylene ethyl acrylate (EEA), ethylene acrylic acid (EAA), ethylene methyl acrylate (EMA), ethylene butyl acrylate (EBA), polyester (PET), polyamide (PA), for example nylon, ethylene vinyl alcohols (EVOH), polystyrene (PS), polyurethane (PU), and thermoplastic olefin elastomers.

Preferred materials for the precursor film web are polyolefins, such as LDPE, LLDPE and PP. Most preferred materials are mixtures of these polymers, such as mixtures of LDPE and LLDPE, mixtures of LDPE or LLDPE and PP, or mixtures of PE or PP with different melting points.

The precursor nonwoven web is also produced in known manner. All nonwoven fabrics containing at least one formulation component based on a thermoplastic polymer are useful. The nonwovens may contain fibers of PE, PP, PET, Rayon, cellulose, PA, and mixtures of these fibers. It is also possible to use bicomponent or multicomponent fibers. Most preferred materials are, for example, nonwovens made of spun or staple fibers based on PP, PE or PET, as well as nonwovens made of mixtures of PP and PE or mixtures of PET and PP or PE.

In general, the thermal lamination method according to the invention can be utilized with all thermoplastic formulations, wherein the melting points and raw materials must be coordinated with each other, as is the case with the thermobonding method. In general, the webs to be laminated must comprise a similar morphology in at least one formulation component, in order to achieve a reliable basis for adequate composite adhesion through temperature.

The number of webs to be laminated is not limited; however, the necessary heating of the webs, for example through a heating cylinder, must be ensured before said webs reach the cooled nip. It is not only possible to laminate nonwovens with films, but also any conceivable combination (e.g. nonwoven-nonwoven; nonwoven-film-nonwoven; film-film; etc.).

The precursor webs may have been produced by any known method, but must contain thermoplastic components. Here, it is important to coordinate the materials of film and nonwoven with each other, on the one hand by choosing crystallite melting points which are sufficiently spaced apart from each other and, on the other hand, by choosing materials which are sufficiently compatible with each other to allow bonding. The appropriate material combinations are known to those skilled in the art and can also be determined by means of a few orienting tests.

The difference in the crystallite melting point of the precursor film web or the low-melting component of the precursor film web should be at least about 5° C., preferably at least about 10° C., and most preferably at least about 20° C. below the melting temperature of the precursor nonwoven web or below the melting temperature of the high-melting component of the precursor nonwoven web.

To achieve a better compatibility, a low-melting component may be contained in the precursor film web or the precursor nonwoven web or in both thereof. Herein, it must be ensured that at least one component of the precursor nonwoven web comprises a melting point above the crystallite melting temperature of the precursor film web or of the lower-melting component in the precursor film web.

To improve material compatibility, it is also possible to use two-layer or multi-layer nonwovens where the layer in the laminate that is in contact with the precursor film web consists of a lower-melting material or contains a lower-melting material than the further layer(s).

According to the invention, the precursor film web and the precursor nonwoven web are jointly heated through a preferably antistick-coated heating cylinder and are then guided through a cooled nip. As a matter of course, it is also possible to use a plurality of heating cylinders or other heating methods, such as infrared radiators. For reasons of clarity, however, the invention will be described below with regard to one heating cylinder only.

In a preferred embodiment, the precursor nonwoven web is in direct contact with the surface of the heating cylinder. The precursor film web is carried along on top thereof. The temperature of the heating cylinder is selected such that the precursor film web is heated up to the molten state across the wrap distance of the heating cylinder, however, such that this temperature does not yet initiate the molten state for the carried-along precursor nonwoven web, i.e. this temperature must be below the crystallite melting point of the precursor nonwoven web.

Since the nonwoven web that is not in the molten state yet bears on the heating cylinder, it is ensured that the molten film web resting on top thereof can be detached in an easy manner that is highly stable with regard to the process.

It is, however, also possible to apply the method with the film web having direct contact to an antistick-coated heating cylinder and a nonwoven web arranged on top thereof.

In the following cooled nip, the laminate is cooled to temperatures below the crystallite melting point of the film web. Preferably, the cooled nip consists of a steel roller and a counterpressure rubber roller. The steel roller is, preferably, provided with a textile-type engraving which further supports the textile appearance of the laminate surface. The preferably used embossed texture of the steel roller reduces the degree of gloss of the laminate.

Contrary to known thermobonding lamination methods wherein two heated steel rollers (raised engraved roller and smooth counterpressure roller) are used to guide a film web and a nonwoven web and the composite is created through temperature and very high pressures in a localized manner only, the thermal lamination method according to the invention provides full-surface lamination. Similar to the known adhesive lamination methods, this is to advantage in that, owing to low pressures in the lamination process (pressureless heating, lamination step in the cooled nip over the entire surface and with soft rubber roller as counterpressure roller), very soft laminates (similar to adhesive laminates) are created without use of adhesives and, on the other hand, the risk of material damage (perforations, pinholes) incurred with thermobonded laminates is excluded.

The composite adhesion between nonwoven and film can very easily be controlled through the degree of heating. The higher the temperature of the surface of the heating cylinder, the higher the composite values between nonwoven and film. The heating process window at the minimum temperature is provided through the absolutely necessary molten state of the raw material component responsible for composite adhesion. The upper heating limit is provided through the crystallite melting point of the nonwoven web. If heating goes beyond the crystallite melting point of the nonwoven web, the resulting laminates will have an indestructible bond between the nonwoven web and the film web; however, the high softness of the laminate will be lost, causing the risk of holes similar to the direct extrusion or thermobonding methods.

Contrary to the known adhesive lamination methods, the thermal lamination method according to the invention is to advantage in that a high softness of the products is achieved without the use of an adhesive. Moreover, said method allows the production of trilaminates (nonwoven-film-nonwoven) without requiring major modifications to the plant. In this case, it is only necessary to carry along a second nonwoven web over the two initial webs and to also heat said web through a heating cylinder or heating cylinders.

As compared with the classic thermobonding method, the thermal lamination method is to advantage in that the produced laminates have a higher softness and material damage caused by high pressures and temperatures is avoided. As a result, these laminates are not associated with the risk of perforations or microholes ("pinholes") which represent a considerable defect in personal hygiene articles (leaky diapers), for example when such laminates are used as backsheets.

As compared with laminates produced according to the known direct extrusion method, the combined nonwoven-film laminates provide a higher softness while the risk of defective spots (perforations, pinholes) is clearly reduced. With direct extrusion, the melt film is applied to the nonwoven directly downstream of the slot die and at extrusion temperature. The nonwoven-film web composite is produced in a subsequent cooled nip. Owing to the necessary high extrusion temperatures (e.g. approx. 230° C. for LDPE-LLDPE-PP mixtures, corresponding to approx. 70° C. above the crystallite melting point of the highest-melting formulation component), the molten film web has a very low viscosity when it is applied to the nonwoven web. In combination with the subsequent cooled pressure-controlled nip, the low-viscosity film web penetrates the nonwoven web to a very high extent. As a result, the laminate is hardened and the nonwoven filaments pierce the film web, this in turn being a cause of perforations and pinholes in the finished product.

Contrary thereto, the invention allows highly precise adjustment of the viscosity of the molten film web by means of the heating cylinder. By decoupling the extrusion and lamination procedure, the high extrusion temperatures can be restricted to this procedure and substantially lower temperatures can be used for the lamination procedure. Contrary to the direct extrusion method (with identical formulations), the invention, hence, allows lamination with the composite values usually required for personal hygiene articles (>0.10 N/cm) as early as when the crystallite melting point of the raw material component in the film web responsible for the lamination behavior is reached.

As compared with direct extrusion lamination, the present invention is further to advantage in that the laminates produced according to the invention can be printed. According to the invention, the film can be printed after the extrusion procedure and before the lamination procedure. This allows printing on the film side which will be covered by the nonwoven in the future laminate. This results in an excellent printing quality, because it is possible to print on the smooth film web. The nonwoven which, in the finished laminate, will be arranged directly on top of said smooth film web affects the print image only to an inconsiderable degree, but will prevent abrasion of the printing ink in the finished product. If the laminates printed according to the invention are, for example, used as backsheets for diapers, the surround cannot become dirty through abrasion of the printing ink, since the latter is covered by the nonwoven.

As regards breathable laminates, this embodiment is further to advantage in that the stretching step for creating the breathability in filler-containing films is, preferably, also achieved before the printing and lamination procedures. This prevents the print subjects from being distorted while stretching is in progress.

With direct extrusion (the molten film web is bonded to the nonwoven web directly downstream of the slot die), it is not possible to print on the film web nor to cover same with the nonwoven web. With this method, it is either possible to print on the nonwoven side (=external surface of the various finished products (e.g. diapers)), this allowing only a highly restricted printing quality and posing the danger of printing ink abrasion in the finished product. Or the side facing the film can be printed before the film is applied, but then the printing quality will remain poor and printing on the nonwoven requires a great amount of printing ink. Further, direct extrusion laminates can be printed by printing on the film side according to what is called the counter print method. Therein, the print subject is visible through the nonwoven and film layers in the finished product. In this case, the print subject can be seen to a limited degree only or not at all; this is particularly applicable to strongly dyed opaque films (for example chalk-filled breathable films).

As a matter of course, the method according to the invention can immediately follow the production of the precursor film web, for example by extruding a film web through a slot system and cooling by means of a stamping unit, a chill-roll system or even a cooling roller or cooling rollers only. Such a system is then equipped with one or more downstream heating cylinders according to the invention with subsequent cooled nip. If desired, a printing unit is installed upstream of the heating cylinder(s) according to the invention.

In a further preferred embodiment, the nonwoven-film combination is, after the lamination procedure, subjected to a ring-rolling step in crossways direction to the web. On the one hand, this stretching in crossways direction (CD) reduces the base weight of the laminate, broadens the web in crossways direction and increases the softness of the finished product. These described changes in property can be easily manipulated through the geometry used and through the degree of engagement of the ring-rolling rollers. As a matter of course, the laminates can also be subjected to a ring-rolling step in machine direction (MD) or in crossways and machine direction (CD+MD). Since the depth of penetration of the film web into the nonwoven web can be easily controlled through the heating cylinder, the formation of perforations and/or pinholes in the stretching procedure can be easily prevented.

FIG. 1 is a schematic diagram of the thermal lamination method according to the invention. A precursor nonwoven web 2 is guided over the deflection roller 3 and a precursor film web 1 is guided over the deflection and impression roller 4. Said webs 2 and 1 are both guided onto a heating cylinder 5. There, the two webs are jointly heated to a temperature above the crystallite melting point of the precursor film web and below the crystallite melting point of the precursor nonwoven web. Therein, the nonwoven web is bearing on the cylinder 5. Subsequently, the composite formed on the heating cylinder 5 is fixed and cooled in the stamping unit which consists of the stamping roller 6 and the rubber roller 7. The composite is guided over the deflection rollers 8 and 9 and is then subjected to a stretching step which is achieved in crossways direction through the ring-rolling rollers 10 and 11. Thereafter, the finished laminate can be further processed in known manner.

The examples following below are intended to illustrate the invention, however without restricting it thereto.

EXAMPLE 1

Nonwoven-Film Laminate (Non-Breathable)

A precursor film web consisting of 30% polypropylene (melting point ranging from 137 to 143° C.), 60% LDPE and 10% LLDPE is blow-extruded in 14 g/m². Thereafter, the precursor film web and a precursor nonwoven web (14 g/m²) based on polypropylene are jointly fed to a system, such as it is schematically represented in FIG. 1. The polypropylene of the film web differs from the polypropylene of the precursor nonwoven web in that its DSC crystallite melting point is approx. 20° C. lower. The precursor nonwoven web is in direct contact with the surface of the heating cylinder. The precursor film web is carried along on top thereof. The temperature of the heating cylinder is selected such that, over the wrap distance of the heating cylinder, the precursor film web is heated up to the molten state at a temperature ranging from 137 to 143° C. At this temperature, the carried-along precursor nonwoven web does not reach the molten state yet. In the subsequent cooled nip, the laminate is cooled down to a value below the crystallite melting point of the film web.

The laminate showed composite values of >0.10 N/cm as required for personal hygiene articles.

EXAMPLE 2

Nonwoven-Film Laminate (Non-Breathable)

A precursor film web consisting of 70% LDPE (melting point ranging from 108 to 113° C.) and 30% LLDPE (117 to 124° C.) is blow-extruded in 14 g/m². Thereafter, the precursor film web and a precursor nonwoven web (14 g/m², melting point ranging from 131 to 135° C.) based on polypropylene are jointly fed to a system, such as it is schematically represented in FIG. 1. The LDPE of the film web differs from the polypropylene of the precursor nonwoven web in that its DSC crystallite melting point is approx. 20° C. lower. The precursor nonwoven web is in direct contact with the surface of the heating cylinder. The precursor film web is carried along on top thereof. The temperature of the heating cylinder is selected such that, over the wrap distance of the heating cylinder, the precursor film web is heated up to the molten state at a temperature ranging from 114 to 125° C., either in part (above LDPE melting point) or as a whole (above LDPE and LLDPE melting points). At this temperature, the carried-along precursor nonwoven web does not reach the molten state yet. In the subsequent cooled nip, the laminate is cooled down to a value below the crystallite melting point of the film web. To achieve an appropriate composite, the molten state of the LDPE formulation component is already sufficient.

The laminate showed composite values of >0.10 N/cm as required for personal hygiene articles.

EXAMPLE 3

Nonwoven-Film Laminate (Breathable)

A precursor film web (precursor film) is blow-extruded. The formulation of the film web consists of 70% polypropylene compound (melting point ranging from 137 to 143° C.) and 30% LLDPE compound (117 to 124° C.) wherein the compounds each consist of a mixture of raw material plus 60% $CaCO_3$ (chalk). Thereafter, the precursor film web and a precursor nonwoven web (14 g/m²) based on polypropylene are jointly fed to a system, such as it is schematically represented in FIG. 1. The polypropylene present in the film web differs from the polypropylene of the precursor nonwoven web in that its DSC crystallite melting point is approx. 20° C. lower. The two webs are jointly heated through an antistick-coated heating cylinder and then guided through a cooled nip (stamping roller and a counterpressure rubber roller) The precursor nonwoven web is in direct contact with the surface of the heating cylinder. The precursor film web is carried along on top thereof. The temperature of the heating cylinder is selected such that, over the wrap distance of the heating cylinder, the precursor film web is heated up to the molten state at a temperature ranging from 137 to 143° C., but that the carried-along precursor nonwoven web does not reach the molten state yet at this temperature. In the subsequent cooled nip, the laminate is cooled down to a value below the crystallite melting point of the film web.

In the present exemplary embodiment, the nonwoven-film combination is, after the lamination procedure, additionally subjected to a ring-rolling step in crossways direction to the material web. This stretching step is intended to generate breathability. That means that fine pores are formed around the chalk grains (mean particle size ranging from 0.8 to 3.0 μm) for achieving breathability, the maximum permissible size of said pores being approx. 1 μm to preserve liquid tightness. The measurement as to ASTM E 398 (38° C., 90% relative air humidity, measuring instrument LYSSY L 80-5000 Lyssy AG, CH) resulted in a permeability to water vapor ranging from 2200 to 2500 g/m² in 24 h.

Depending on the size of the chalk grains used and the ring-rolling penetration depth, a permeability to water vapor ranging from 500 to 3500 g/m² in 24 h can be achieved.

EXAMPLE 4

Nonwoven-Film Laminate (Highly Breathable)

In a first step, a precursor film web (precursor film) is blow-extruded. The formulation of the film web consists of 70% low-melting polypropylene compound (melting point approx. at 130° C.) and 30% high-melting polypropylene compound (melting point ranging from 158 to 164° C.). The compounds each consist of a mixture of raw material plus 55% $CaCO_3$ (chalk).

After the so-called precursor film has been blow-extruded, the film is stretched in machine direction in a monoaxial MDO stretching unit. Therein, 100% of the film web is stretched in machine direction with the stretching degree ranging from 1:1.5 to 1:4.0, thus producing breathability. Contrary to partial stretching in ring-rolling, MDO stretching allows to reach very high breathabilities without posing the risk of perforations or pinholes and, thus, of film webs that are permeable to liquid; this is achieved by means of high stretching degrees and owing to the fact that the entire film web area is available for stretching.

After completion of the stretching step, the breathable film web can be very easily printed if desired, using the usual methods. The smooth film surface provides the basis of highly precise print images on the film web, and the print subjects are preserved, showing no distortions caused by the previous stretching step. For example, breathable direct extrusion laminates (nonwoven-film laminates) are not stretched before printing on the nonwoven web and the lamination procedure are completed. Therein, the print subjects are distorted through this following stretching step.

Subsequently, the breathable film web and a precursor nonwoven web (14 g/m$^2$) based on polypropylene are jointly heated through an antistick-coated heating cylinder and then guided through a cooled nip. The polypropylene present in the film web differs from the high-melting polypropylene of the precursor nonwoven web in that its DSC crystallite melting point is approx. 20° C. lower. In two nonwoven layers, the formulation of the three-layer precursor nonwoven web consists of a high-melting polypropylene (crystallite melting point ranging from approx. 150 to 165° C.). Similar to the film web, the third nonwoven layer (=external surface=lamination side facing the film) was made of a polypropylene having a melting point of approx. 130° C.

The precursor nonwoven web is in direct contact with the surface of the heating cylinder, wherein the nonwoven layer having the reduced melting point faces the precursor film web. The precursor film web is carried along on top thereof. The temperature of the heating cylinder is selected such that, over the wrap distance of the heating cylinder, the precursor film web is, in part, heated up to the molten state of the low-melting PP compound, but such that this temperature (ranging from 130 to 140° C.) does not cause the carried-along precursor nonwoven web to reach the molten state of the two high-melting PP nonwoven layers yet. Therein, the third low-melting PP nonwoven layer is heated up to the crystallite melting point. This nonwoven layer is in direct contact with the precursor film web and supports an appropriate composite (>0.10 N/cm) through the molten state. In the subsequent cooled nip, the laminate is cooled down to a value below the crystallite melting point of all formulation components of the film and nonwoven webs. A permeability to water vapor ranging from 2000 to 3500 g/m$^2$ in 24 h has been measured.

As in example 2, it is also possible to manipulate the permeability to water vapor by means of the parameters of filler particle sizes and ring-rolling penetration depth. Values ranging from 500 to 5000 g/m$^2$ are possible.

Additional ring-rolling in crossways direction further increases the softness and the permeability to water vapor.

The invention claimed is:

1. A method for the production of nonwoven-film laminates for personal hygiene articles consisting of a film web made of a thermoplastic polymer and a nonwoven web, the method comprising:
    a) providing a film web made of a thermoplastic polymer;
    b) providing a nonwoven web, wherein the nonwoven web has a melting point in excess of the crystallite melting point of the thermoplastic polymer;
    c) jointly heating the film web and the nonwoven web to a temperature above the crystallite melting point of the thermoplastic polymer and below the melting point of the nonwoven web, in order to heat the film web to a molten state and form the nonwoven-film laminate; and
    d) guiding the nonwoven-film laminate through a cooled nip in order to cool the nonwoven-film laminate below the crystallite melting point of the film web, wherein the heating comprises wrapping the film web and the nonwoven web around a heating cylinder a wrap distance so that the film web is heated to the molten state.

2. The method according to claim 1, wherein the cooled nip is formed by a stamping roller and a rubber roller, wherein the embossed texture of the stamping roller reduces the degree of gloss of the laminate.

3. The method according to claim 1, wherein the cooled laminate is subjected to a stretching step in machine direction or crossways direction or in machine direction and crossways direction.

4. The method according to claim 1, wherein the film web is blow-extruded.

5. The method according to claim 1, wherein the film web is printed.

6. The method according to claim 1, wherein the film web is stretched in machine direction or crossways direction or in machine direction and crossways direction.

7. The method of claim 1, wherein the nonwoven web is in direct contact with the heating cylinder.

* * * * *